US00PP17934P3

(12) United States Plant Patent
Delabroye

(10) Patent No.: US PP17,934 P3
(45) Date of Patent: Aug. 21, 2007

(54) ***HEUCHERA* PLANT NAMED 'CITRONELLE'**

(50) Latin Name: *Heuchera villosa*
Varietal Denomination: Citronelle

(76) Inventor: Sandrine Delabroye, Rue Roger Salengro 40, Hantay (FR), F-59496

( * ) Notice: Subject to any disclaimer, the term of this patent is extended or adjusted under 35 U.S.C. 154(b) by 0 days.

(21) Appl. No.: 11/291,373

(22) Filed: Dec. 1, 2005

(65) Prior Publication Data

US 2007/0130662 P1 Jun. 7, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of *Heuchera villosa,* 'Citronelle', a sport of *Heuchera villosa* 'Caramel', characterized by its uniquely colored yellow-green foliage, its cordate-shaped leaves on rosy red petioles, its vigorous growth habit and its resistance to disease.

2 Drawing Sheets

Botanical classification: *Heuchera villosa.*
Cultivar designation: 'Citronelle'.

BACKGROUND OF THE INVENTION

The present invention relates to a new and distinct cultivar of *Heuchera villosa,* and is hereinafter referred to by the cultivar name 'Citronelle'.

The inventor discovered the new cultivar, 'Citronelle' as a naturally occurring sport of *Heuchera villosa* 'Caramel' (U.S. Plant Pat. No. 16,560) in a cultivated nursery bed in Hantay, France, CT in July of 2005.

The new cultivar was selected for its unique foliage that is bright yellow-green in color, the color is retained throughout the growing season. The foliage of the parent plant, 'Caramel', emerges grey-red in color and matures to a golden yellow-green color. 'Citronelle' is similar to the parent plant in all other characteristics.

Asexual reproduction of the new cultivar was first accomplished under direction by the inventor by in vitro propagation in Rijswijk, The Netherlands in August of 2005. Asexual reproduction of the new cultivar by division and tissue culture has shown that the unique features of 'Citronelle' are stable and reproduced true to type in successive generations.

SUMMARY OF THE INVENTION

The following traits have been repeatedly observed and represent the characteristics of the new cultivar. These attributes in combination distinguish 'Citronelle' as a new and unique cultivar of *Heuchera.*

1. 'Citronelle' has foliage that is yellow-green in color. The foliage emerges yellow-green and the foliage coloration is retained throughout the growing season.
2. The leaves of 'Citronelle' are cordate in shape and fairly flat in aspect on greyed-red petioles.
3. 'Citronelle' reaches a height of about 12 cm and a spread of about 28 cm.

4. 'Citronelle' is vigorous grower in comparison other *Heuchera* with colored foliage and has been shown to be resistant to diseases under the conditions tested.

'Citronelle' differs from the parent plant 'Caramel' in foliage color. The foliage of 'Caramel' emerges grey-red in color (176A with margins of 177B) and matures to a golden yellow green (152A to 152B with an overlay of 199A) whereas the foliage color of 'Citronelle' is yellow-green (150B) through the growing season without any brown overlay as exhibited in 'Caramel'. 'Lime Rickey' (U.S. Plant Pat. No. 16,210) is a close comparison plant based on foliage color, however the foliage of 'Lime Rickey' emerges yellow 9A and matures to yellow green 145A to 145B and 'Lime Rickey' is of hybrid origin, whereas 'Citronelle' is a *Heuchera villosa* type and exhibits larger leaves with greater plant vigor. 'Citronelle' can also be compared to *Heuchera villosa* 'Brownies' (Not patented), which is similar in foliage characteristics with the exception of color as 'Brownies' is brown in color rather than yellow-green.

BRIEF DESCRIPTION OF THE DRAWING

The accompanying colored photographs illustrate the overall appearance and distinct characteristics of the new *Heuchera.* The photographs were taken in The Netherlands in August of a one year-old plant as grown outdoors in a one gallon container.

The photograph on FIG. 1 provides an overall view of foliage characteristics of new cultivar.

Figure 1:
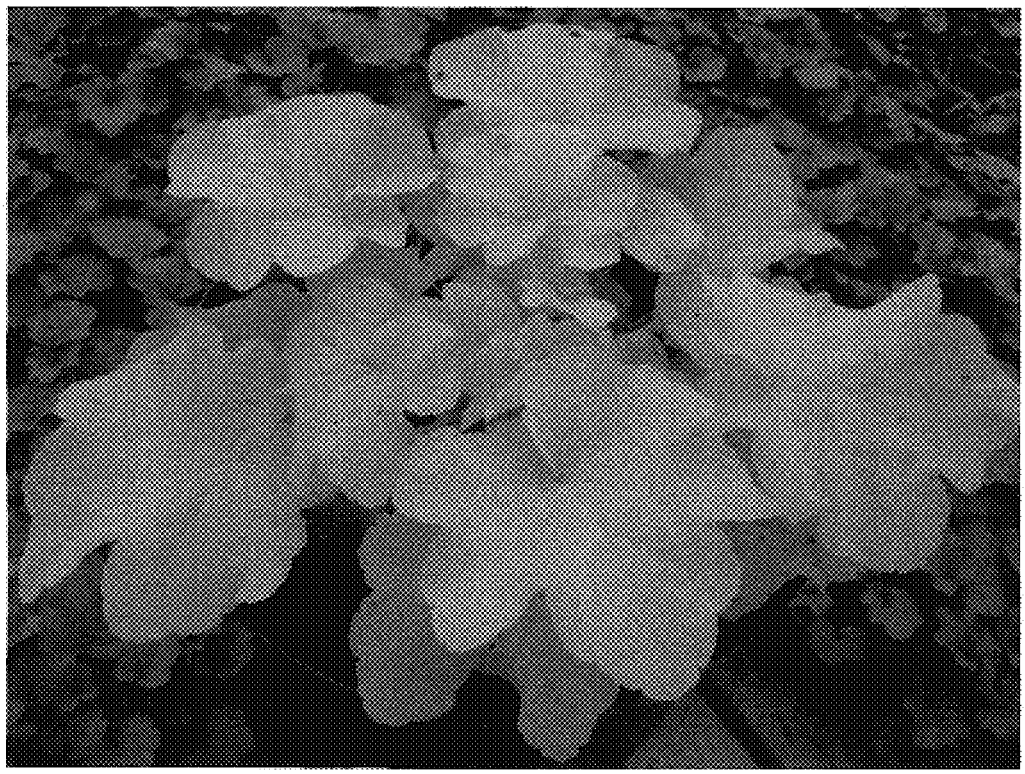
Figure 2:
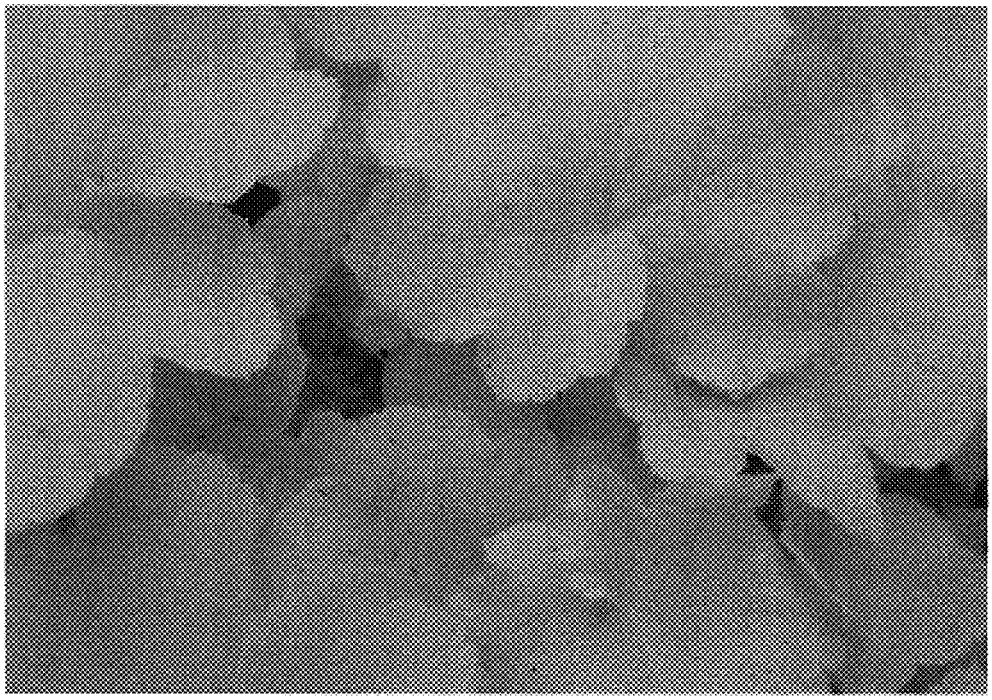
Figure 3:
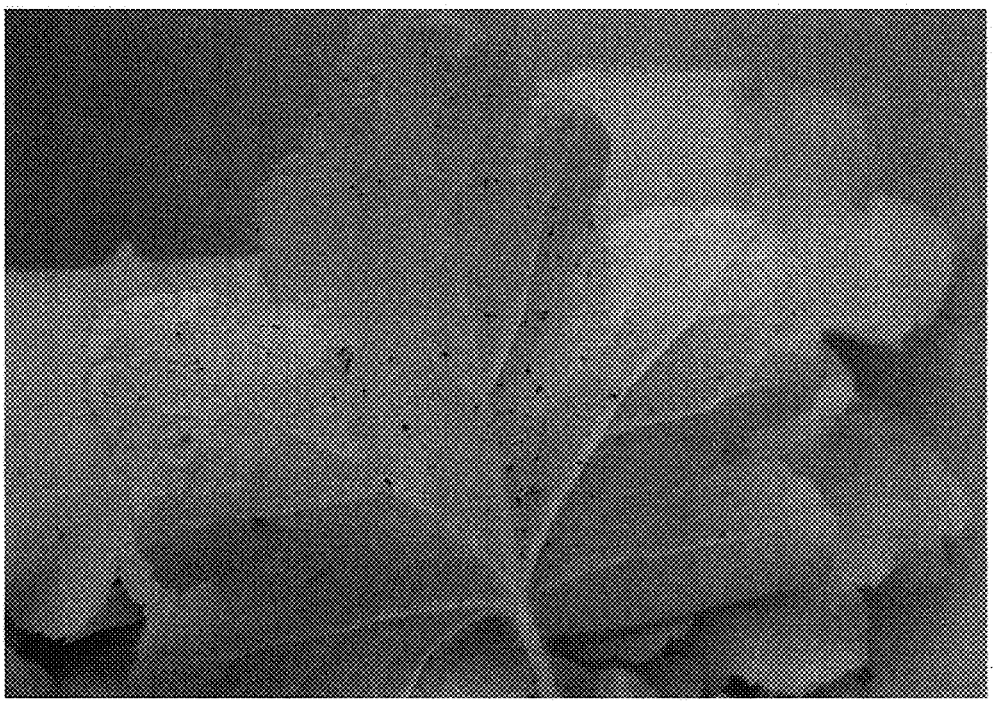

The photographs in FIG. 2 is a close-up view of the foliage of 'Citronelle' and the photograph in FIG. 3 is a close-up view of the lower surface of a mature leaf of 'Citronelle'.

The colors in the photographs are as close as possible with the photographic and printing technology utilized. The color values cited in the detailed botanical description accurately describe the colors of the new *Heuchera.*

DETAILED BOTANICAL DESCRIPTION OF THE PLANT

The following is a detailed description of a one year-old plant of the new cultivar as grown outdoors in The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Citronelle' is a cultivar of *Heuchera villosa.*

Parentage: Naturally occurring sport of *Heuchera* 'Caramel'.

General description:

*Plant habit.*—Clump-forming herbaceous perennial, mounded foliage.

*Height and spread.*—Reaches about a height of about 12 cm in height and about 28 cm in width.

*Hardiness.*—Cold hard to at least U.S.D.A. Zone 6.

*Culture.*—Full sun to medium shade in moist, well-drained, fertile soils.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Root initiation.*—Roots appear in rooting media in 10 day at 20° C. in the laboratory without supplemental lighting.

*Root development.*—Rooted transplants from tissue culture fully develop in a 2.5 in container in about 20 days in a greenhouse with average temperatures of about 20° C. without supplemental lighting in The Netherlands.

*Growth rate.*—Vigorous compared to what is typically observed for *Heuchera* with colored foliage. A 2.5-inch container will fully develop in a one-gallon container in 2 to 2.5 months in the Netherlands.

Foliage description:

*Leaf shape.*—Cordate.

*Leaf division.*—Simple, but lobed with about 5 to 7 lobes per leaf.

*Leaf base.*—Strongly cordate (leaves at base overlap).

*Leaf apex.*—Acute to rounded.

*Leaf venation.*—Primary palmate, secondary net-veined, not conspicuous, vein color on upper surface matched leaf color, vein color on lower surface of mature leaves is 145D.

*Leaf margins.*—Crenate.

*Leaf attachment.*—Petiolate.

*Leaf arrangement.*—Basal rosettes.

*Leaf orientation.*—Held horizontal to petiole, held nearly flat (not ruffled or curled).

*Leaf surface.*—Upper and lower; pubescent with 1 mm stiff white hairs.

*Leaf color.*—Young and mature leaves, upper surface; 150B. Young and mature leaves, lower surface; 145A to 145C.

*Leaf size.*—About 8 cm in length, up to about 7.5 cm in width.

*Leaf quantity.*—About 11 per basal rosette.

*Petiole size.*—About 9 cm in length, about 2 mm in width.

*Petiole color.*—182C (greyed-red), occasionally 145C (yellow-green) especially near leaf attachment.

*Petiole shape.*—Round.

*Stipules.*—2 leafy stipules at the base of each petiole, oblong in shape, 1 cm in length, 2 mm in width, color 182C (both surfaces), margins sparsely covered with short hairs.

Flower and seed description: Flowering has not been observed on the plants under the conditions tested.

I claim:

1. A new and distinct cultivar of *Heuchera* plant named 'Citronelle' as herein illustrated and described.

* * * * *